(12) United States Patent
Chu et al.

(10) Patent No.: US 11,653,827 B2
(45) Date of Patent: May 23, 2023

(54) MEDICAL SYSTEMS, DEVICES, AND RELATED METHODS

(71) Applicant: Boston Scientific Scimed, Inc., Maple Grove, MN (US)

(72) Inventors: Michael S. H. Chu, Brookline, MA (US); Sacha Tang, Lowell, MA (US); Mayur Kiran Patel, Framingham, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 739 days.

(21) Appl. No.: 16/663,751

(22) Filed: Oct. 25, 2019

(65) Prior Publication Data
US 2020/0197579 A1   Jun. 25, 2020

Related U.S. Application Data

(60) Provisional application No. 62/783,034, filed on Dec. 20, 2018.

(51) Int. Cl.
| | |
|---|---|
| *A61M 25/00* | (2006.01) |
| *A61B 17/00* | (2006.01) |
| *A61M 1/00* | (2006.01) |
| *A61B 1/307* | (2006.01) |
| *A61B 18/26* | (2006.01) |
| *A61B 18/00* | (2006.01) |
| *A61B 17/22* | (2006.01) |

(52) U.S. Cl.
CPC .............. *A61B 1/307* (2013.01); *A61B 18/26* (2013.01); *A61M 25/0097* (2013.01); *A61B 2017/0034* (2013.01); *A61B 2017/00292* (2013.01); *A61B 2017/22079* (2013.01); *A61B 2018/00982* (2013.01); *A61B 2217/005* (2013.01); *A61M 1/772* (2021.05); *A61M 25/0069* (2013.01); *A61M 2025/0004* (2013.01); *A61M 2025/0025* (2013.01)

(58) Field of Classification Search
CPC .. A61M 2025/0025; A61M 2025/0034; A61B 1/00135; A61B 1/00131
See application file for complete search history.

(56) References Cited

U.S. PATENT DOCUMENTS

| | | | | |
|---|---|---|---|---|
| 2006/0235458 | A1* | 10/2006 | Belson | A61B 1/00135 606/191 |
| 2007/0060889 | A1* | 3/2007 | Adams | A61B 17/3415 604/164.01 |
| 2010/0249639 | A1* | 9/2010 | Bhatt | A61M 16/0436 128/207.14 |
| 2014/0052097 | A1* | 2/2014 | Petersen | A61M 25/0069 604/528 |
| 2016/0135666 | A1* | 5/2016 | Hashimoto | A61B 1/0051 600/107 |
| 2017/0319221 | A1* | 11/2017 | Chu | A61B 17/22 |

* cited by examiner

*Primary Examiner* — Elizabeth Houston
*Assistant Examiner* — Lauren Dubose
(74) *Attorney, Agent, or Firm* — Seager, Tufte & Wickhem, LLP

(57) ABSTRACT

A medical system includes an insertion device including a delivery shaft with an internal lumen, a coupling tube coupled to the delivery shaft and configured to receive a medical device, and a liner tube inserted through the internal lumen of the delivery shaft.

15 Claims, 6 Drawing Sheets

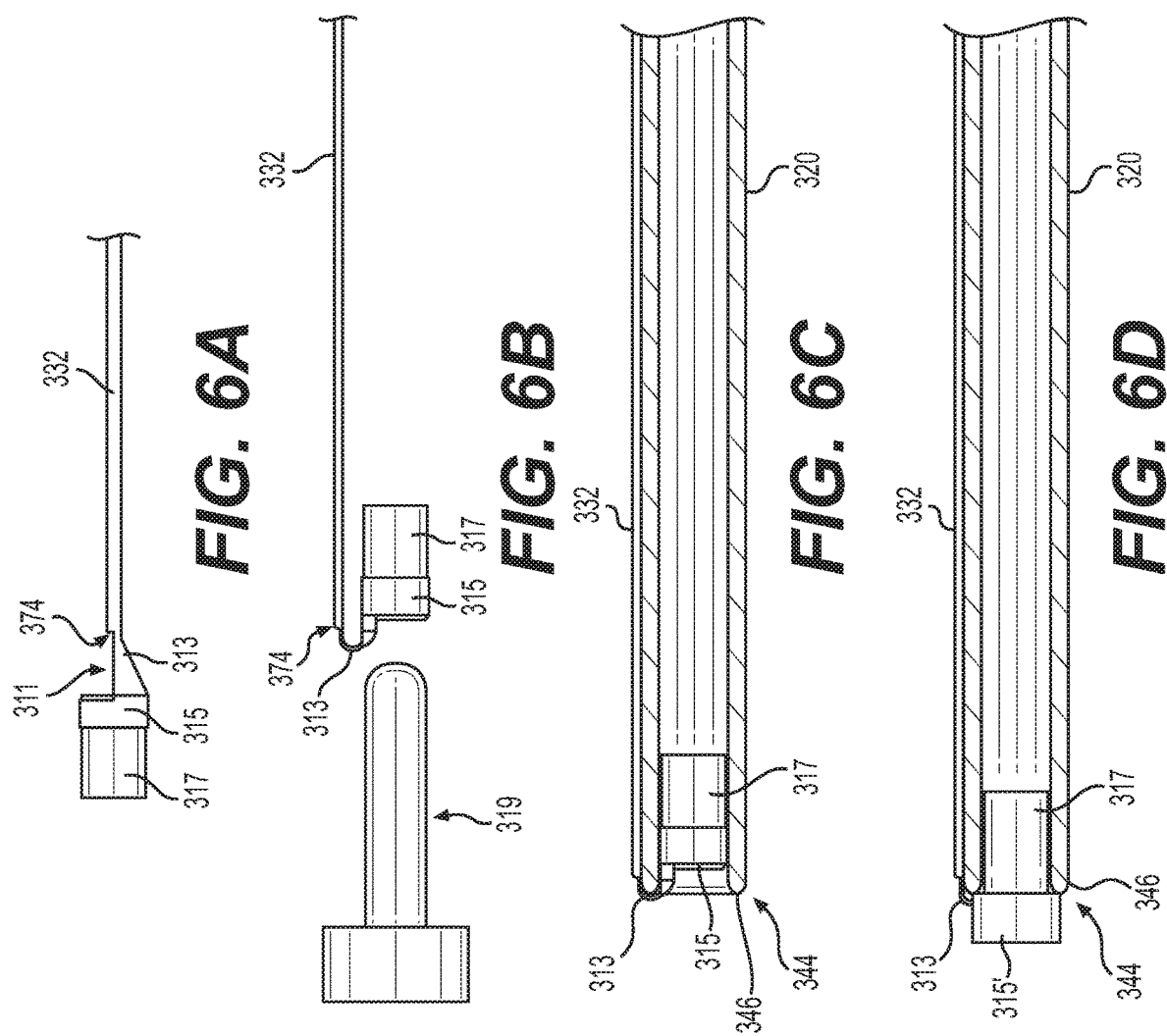

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/783,034, filed Dec. 20, 2018, which is herein incorporated by reference in its entirety.

TECHNICAL FIELD

Various aspects of the present disclosure relate generally to systems, devices, and methods useful in medical procedures. More specifically, the present disclosure relates to systems, devices, and methods for performing a laser lithotripsy procedure with stone dusting.

BACKGROUND

Lithotripsy is a medical procedure involving the physical disruption of a hardened mass within a body cavity, such as kidney stones, gallstones, pancreatic stones, or the like. In such procedures, energy is applied to the hardened mass. Different energy sources may be used, such as electric, hydraulic, laser, mechanical, ultrasound, or the like. Laser lithotripsy is based on the fact that pulsed light energy from an energy delivery device may be converted into a mechanical energy in the form of a cavitation bubble associated with the occurrence of a shock-wave. This mechanical energy may help to disrupt and break up the hardened mass.

Many lithotripsy procedures generate particles or pollution within the body cavity as the hardened mass is disrupted and broken up. For stone-like masses, these particles may be referred to as "stone dust." In laser lithography procedures, this stone dust may hinder visualization of the mass, which may prevent the physician from locating the mass and delivering the laser energy in the most efficient manner. Fluid may be injected into the body cavity so that a portion of the stone dust will naturally drain out of the body cavity with the fluid. Stone dust or other particles may not drain out of certain body cavities or portions of a body cavity, for example, a lower pole of a kidney. Suction may be delivered to the body cavity to help remove the stone dust, but applying suction may require either removing the energy delivery device or inserting an additional medical device into the body cavity, which may prolong the procedure or expose the patient to contamination or other risks. Furthermore, the suction device may be susceptible to clogs or reduced fluid flow if stone dust or other particles accumulate within the suction lumen. The aforementioned risks may increase the cost, time, and necessary personnel for a medical procedure, further complicating and prolonging the procedure, and exposing the patient to greater risk.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

In one example, a medical system may include an insertion device including a delivery shaft with an internal lumen, a coupling tube coupled to the delivery shaft and configured to receive a medical device, and a liner tube inserted through the internal lumen of the delivery shaft.

The medical system may further include one or more of the following features. The coupling tube may include a collapsed configuration and an expanded configuration. The coupling tube may be configured to transition to the expanded configuration upon receiving the medical device, and the coupling tube may be configured to transition to the expanded configuration during delivery of a fluid and to transition to the collapsed configuration during delivery of suction. The coupling tube may be coupled to the delivery shaft via a fitting. A proximal end of the coupling tube may be coupled to a coupling tube plunger, and the fitting may include a fitting housing with a spring biasing the coupling tube plunger. The fitting housing may include a slot, and the coupling tube plunger may include a pin configured to move within the slot.

The medical system may further include an adaptor coupled to a proximal end of the coupling tube plunger, and the adaptor may be configured to form a one-way seal around the medical device. A distal end of the coupling tube may include a distal flap, and the medical system may further include a loop surrounding a distal portion of the delivery shaft and the distal flap. The medical system may further include one or more loops surrounding one or more portions of the delivery shaft and the coupling tube, and the loops may be formed of a heat-shrink or elastic material. A distal end of the coupling tube may include a skived portion and a distal portion. The distal portion of the coupling tube may be coupled to a tube insert, and the tube insert may be positioned within a distal opening of the delivery shaft.

The medical system may further include a tube insert positioned within the distal portion of the coupling tube, and the tube insert may be more rigid than the coupling tube. The insertion device may include a port, and the liner tube may be inserted through and coupled to the port via a connector that forms a seal around the port. The connector may include a liner tube plunger and a liner tube plunger housing. The liner tube plunger may be longitudinally movable within at least a portion of the liner tube plunger housing. The liner tube plunger housing may include a spring biasing the liner tube plunger. The liner tube plunger housing may include a track, and the liner tube plunger may include a pin configured to move within the track. The track in the liner tube plunger housing may include a longitudinally extending channel with one or more slots extending from the channel. The medical system may further include a stylet configured to extend through at least a portion of the liner tube.

In another aspect, a medical system may include an insertion device including a delivery shaft with an internal lumen and a coupling tube coupled to the delivery shaft. The coupling tube may be configured to receive a medical device, and may be configured to transition between a collapsed configuration and an expanded configuration upon receiving the medical device. The coupling tube may be coupled to an exterior of the delivery shaft.

The medical system may further include one or more the following features. The coupling tube may be coupled to the delivery shaft via a fitting. A proximal end of the coupling tube may be coupled to a coupling tube plunger. The fitting may include a fitting housing with a spring biasing the coupling tube plunger, and the fitting housing may include a slot. The coupling tube plunger may include a pin configured to move within the slot.

A distal end of the coupling tube may include a skived portion and a distal portion. The medical system may further include a tube insert, and the tube insert may be more rigid than the coupling tube. The distal portion of the coupling tube may be coupled to the tube insert, and the tube insert may be positioned within a distal opening of the delivery shaft.

In a further example, a method may include inserting a delivery shaft of an insertion device and a coupling tube to a treatment site. The coupling tube may be coupled to an exterior of the delivery shaft of the insertion device, and the coupling tube may be in a collapsed configuration during insertion. The method may further include inserting a liner tube through a lumen in the delivery shaft via a port in a handle of the insertion device, and inserting a medical device through the coupling tube. Inserting the medical device through the coupling tube may transition the coupling tube from the collapsed configuration to an expanded configuration with a lumen that at least partially surrounds the medical device. The method may then include delivering energy through the medical device to break up a kidney stone or a hardened mass, and delivering fluid through the lumen of the coupling tube. The method may also include applying suction through the liner tube, and breaking up a clog or blockage that forms within the lumen of the delivery shaft or within the liner tube.

The method may include one or more of the following features. The step of breaking up the clog or blockage that forms within the lumen of the delivery shaft or within the liner tube may include at least one of extending the liner tube distally via a plunger coupled to a handle of the insertion device, or extending a shaft of a stylet through the liner tube.

Both the foregoing general description and the following detailed description are exemplary and explanatory only and are not restrictive of the features, as claimed. As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," "generally," and "approximately," indicate a range of values within +/−10% of a stated value.

BRIEF DESCRIPTION OF THE DRAWINGS

The accompanying drawings, which are incorporated in and constitute a part of this specification, illustrate various exemplary embodiments and together with the description, serve to explain the principles of the disclosure.

FIGS. 6A-6C illustrate a distal end of an additional coupling tube and mechanisms that may be used to couple the distal end of the additional coupling tube to the distal end of the medical system, and FIG. 6D illustrates another distal end of the additional coupling tube and mechanism that may be used to couple the distal end of the additional coupling tube to the distal end of the medical system, according to aspects of the present disclosure.

DETAILED DESCRIPTION

Examples of the present disclosure include systems, devices, and methods to facilitate and improve the efficacy, efficiency, and safety of medical procedures to break up and remove hardened masses. For example, aspects of the present disclosure may provide an operator (e.g., a physician, medical technician, or other medical service provider) with the ability to more easily apply laser energy from an energy source to a kidney stone and apply suction to remove stone dust. Aspects of the present disclosure may allow an operator to deliver energy, deliver irrigation, and apply suction within a body cavity, and breakup a clog or blockage within the suction tube without the need to remove medical devices from the body cavity. Some aspects of the present disclosure may be used in performing an endoscopic, hysteroscopic, or ureteroscopic procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or an insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
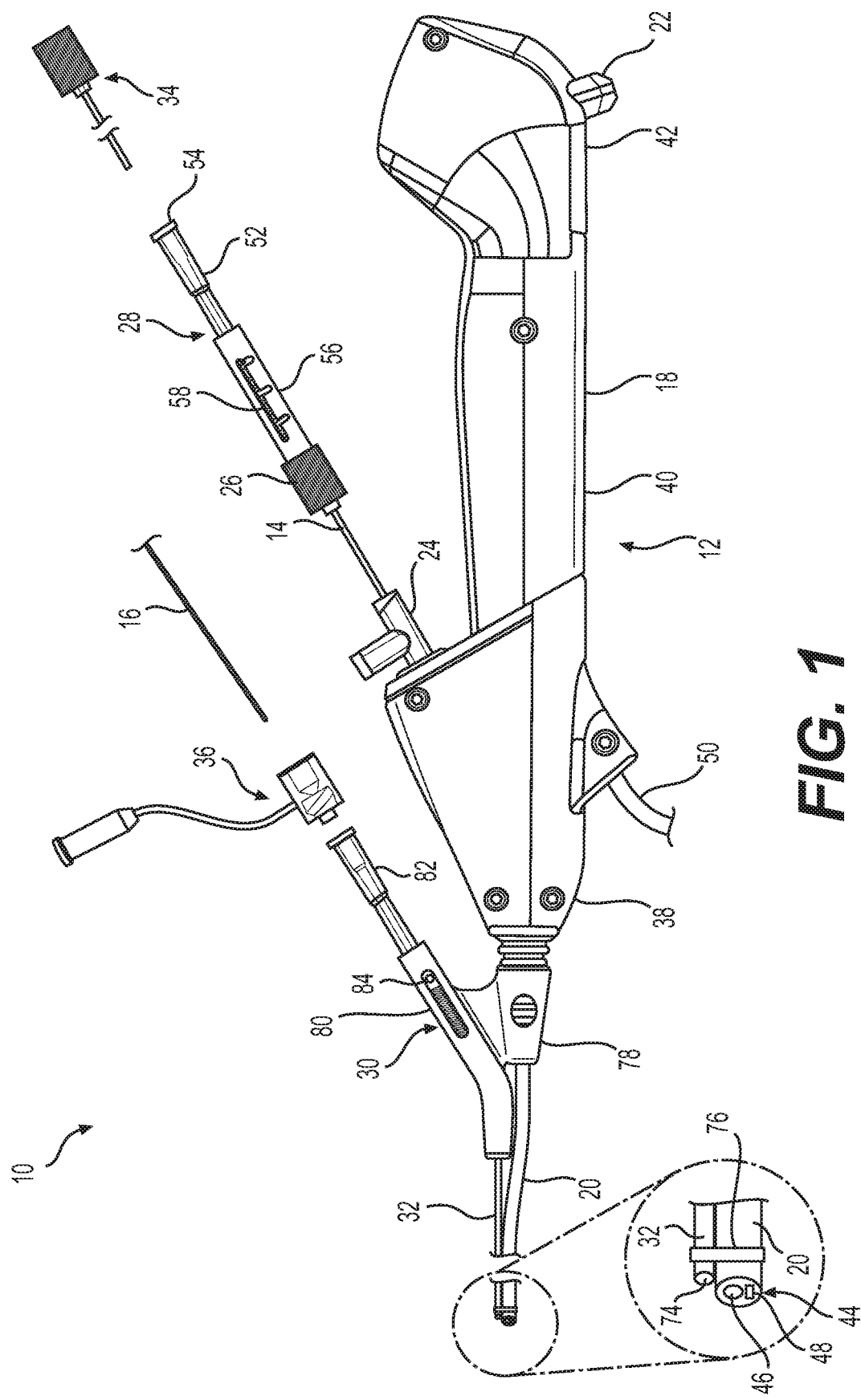
FIG. 1 is a partially exploded view of a medical system according to aspects of the present disclosure.

FIG. 1 illustrates a medical system 10 that includes an insertion device 12, a liner tube 14, and a medical device 16. Insertion device 12 may include a body 18 and a delivery shaft 20. Body 18 may include a deflection lever 22 and at least one port 24. Liner tube 14 may be inserted through port 24 and through delivery shaft 20. Liner tube 14 may be coupled to port 24 via a connector 26, which may include plunger 28. A proximal end of medical device 16 may be coupled to an energy source (not shown) or to another medical device. A distal end of medical device 16 may be coupled to insertion device 12 via a fitting 30 and a coupling tube 32. Fitting 30 may partially surround a portion of delivery shaft 20 or may otherwise be coupled to insertion device 12. Coupling tube 32 may extend distally from fitting 30 and may be coupled to delivery shaft 20 such that medical device 16 may extend through coupling tube 32 and be substantially parallel to delivery shaft 20. Medical system 10 may include a stylet 34, which may be inserted through liner tube 14. Additionally, medical system 10 may include a seal adaptor 36, which may help couple medical device 16 to coupling tube 32.

Insertion device 12 may be a ureteroscope (e.g., Litho-Vue™ Single-Use Digital Flexible Ureteroscope by Boston Scientific Corp.), an endoscope, a hysteroscope, a bronchoscope, a cystoscope, or any similar device. Insertion device 12 may be for single-use and be disposable, or insertion device 12 may be reusable. The body 18 of insertion device 12 may have a distal portion 38, an intermediate portion 40, and a proximal portion 42. Deflection lever 22 may be positioned on a rounded corner of proximal portion 42 and be manipulated to deflect a distal end 44 of the delivery shaft 20. Intermediate portion 40 may be generally a constant diameter, and may form a portion of the insertion device 12 that an operator may grip such that the operator's thumb is proximate the deflection lever 22. The at least one port 24 may be positioned in the distal portion 38. The at least one port 24 may be a T-connector as shown in FIG. 1, may be a Y-connector, or another appropriate connector. Port 24 may be threaded, may be a luer component, and/or may include one or more internal flexible seals. The at least one port 24 may connect to the delivery shaft 20 through at least one internal lumen (not shown) in the body 18 of insertion device 12. Additionally, connector 26 may include an external or internal fitting, such as, for example, a gateway fitting, that may form a seal over port 24 and around liner tube 14.

Insertion device 12 includes an internal lumen with a distal opening 46 in the distal end 44 that connects to port 24 to form a working channel. As such, liner tube 14 may be inserted through port 24 and extended to a position just proximal to distal opening 46, or liner tube 14 may be extended distally beyond distal opening 46. Delivery shaft 20 may include an integral camera and/or an illumination source 48 at distal end 44, and camera and/or illumination source 48 may be connected to a user interface and a display via a communication and power conduit 50 extending from body 18 of insertion device 12.

Liner tube 14 may be coupled to port 24 via connector 26, and may extend through an internal lumen of insertion device 12 such that a distal end of liner tube 14 is approximately flush with or just proximal to distal end 44 of delivery shaft 20. A proximal end of liner tube 14 may be coupled to plunger 28. The proximal end of liner tube 14 may be coupled to a distal end of a plunger body 52 to form a watertight seal around the coupling to allow fluid or material to flow through liner tube 14 into a hollow inner portion of plunger body 52. Plunger body 52 may include a plunger hub 54 at a proximal end. In one aspect, plunger hub 54 may be coupled to a suction source (not shown) in order to provide suction through liner tube 14 and remove stone dust, other particulate, or fluid from the body cavity. Plunger body 52 may be partially surrounded by a plunger housing 56, and plunger housing 56 may extend proximally from connector 26. Plunger housing 56 may include a spring 58 between a distal end of plunger body 52 and connector 26 in order to bias movement of plunger body 52 within plunger housing 56. Accordingly, movement of plunger body 52 within plunger housing 56 may extend or retract liner tube 14 relative to distal end 44.

Figure 2:
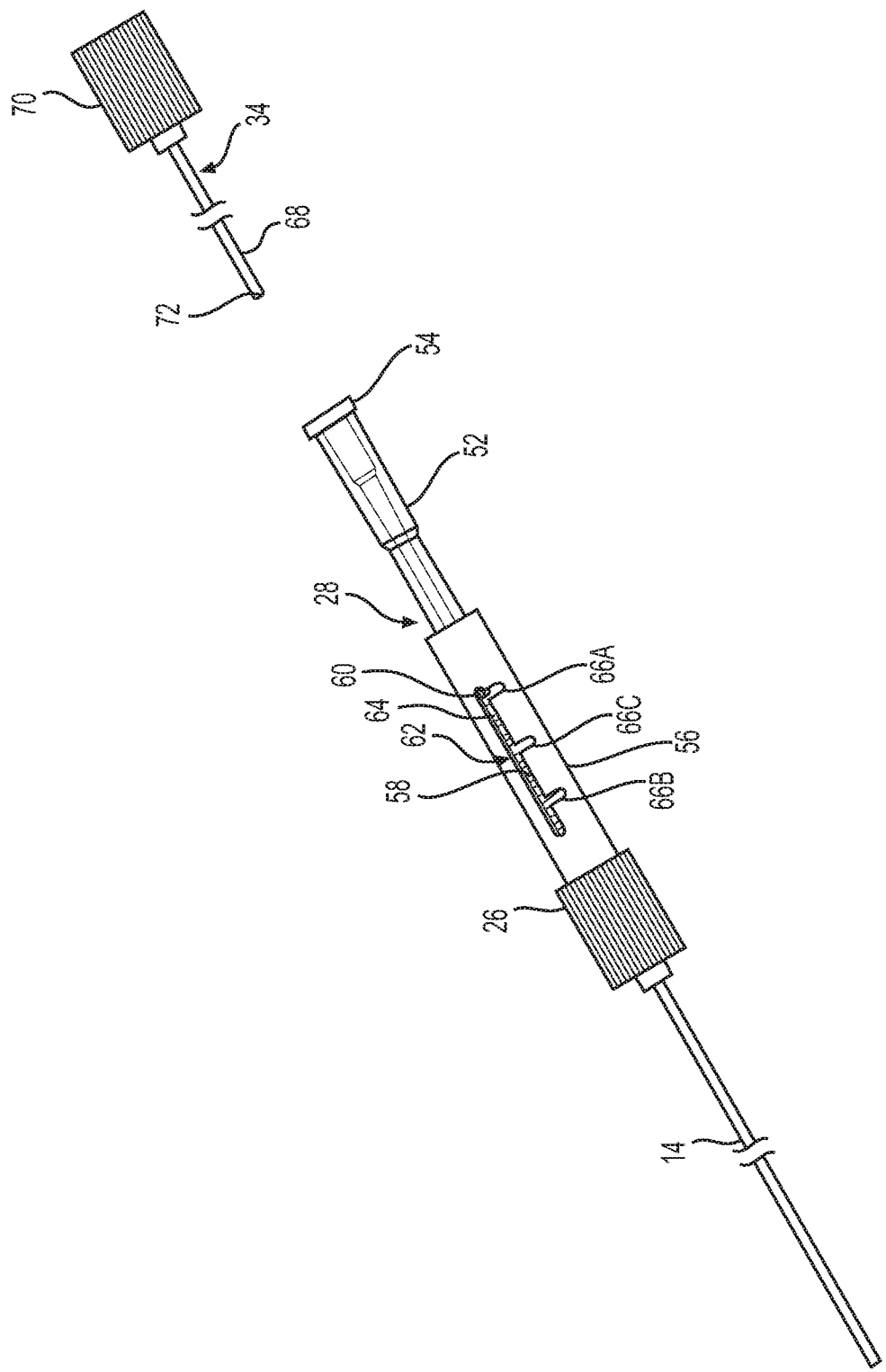
FIG. 2 illustrates a portion of the medical system of FIG. 1, according to aspects of the present disclosure.

As shown in FIG. 2, plunger body 52 may include a pin 60, and plunger housing 56 may include a pin track 62. Pin 60 may be moveable within a pin track 62 during the extension or retraction of plunger body 52 relative to plunger housing 56. Pin track 62 may include a longitudinally extending channel 64 with the one or more slots 66 extending circumferentially around a portion of plunger housing 56 and perpendicular to channel 64. Plunger body 52 may be depressed distally or pulled proximally relative to plunger housing 56 in order to move pin 60 within channel 64.

Additionally, plunger body 52 may be rotated relative to plunger housing 56 in order to position pin 60 in one of slots 66, and thus frictionally secure the longitudinal position of plunger body 52 and liner tube 14. For example, plunger housing 56 may include a proximal slot 66A in order to lock plunger body 52, and thus liner tube 14, in a proximal or retracted position, which may correspond to the distal end of liner tube 14 being proximal of distal end 44 of delivery shaft 20. Plunger housing 56 may include one or more distal slots 66B in order to lock plunger body 52, and thus liner tube 14, in a distal or extended position, which may correspond to the distal end of liner tube 14 being distal of distal end 44 of delivery shaft 20. Plunger housing 56 may include one or more intermediate slots 66C in order to lock plunger body 52, and thus liner tube 14, in an intermediate position, which may correspond to the distal end of liner tube 14 being flush with distal end 44 of delivery shaft 20.

Liner tube 14 may help to protect the working channel of insertion device 12. Additionally, liner tube 14 may be extended distally (via action on plunger body 52) in order to help clear or break up clogs that may form in distal opening 46 or near distal end 44 of delivery shaft 20 during the removal of stone dust. Liner tube 14 may include an outer diameter that is sized to be received within and be movable within the working channel of insertion device 12, for example, slightly smaller than the inner diameter of the working channel. Liner tube 14 may be formed of a thin wall tube, for example, a 0.001 inch thick wall of a polyamide, polytetrafluoroethylene, or another appropriate material. In some aspects, liner tube 14 or a portion of liner tube 14 may include a coil, braid, or additional layers of material in order to reinforce or strengthen portions of liner tube 14, for example, a distal end of liner tube 14. In other aspects, portions of liner tube 14 may not include the reinforcement or strengthening, which may allow those portions of liner tube 14 to be more flexible, for example, in order to deflect with delivery shaft 20 based on the operator's actuation of deflection lever 22.

Furthermore, medical system 10 may include stylet 34. Stylet 34 may include a shaft 68 and a stylet handle 70. Shaft 68 may be sized to fit within the inner diameter of liner tube 14, and may be approximately as long as liner tube 14 and plunger body 52. Shaft 68 may include a distal tip 72, which may be rounded or atraumatic. Stylet handle 70 may be sized to fit over, be screwed onto, or otherwise secured to the proximal end of plunger body 52. Stylet 34 may be inserted into liner tube 14 to help break up or push out a clog or blockage within liner tube 14, in distal opening 46, or near distal end 44 of delivery shaft 20. Stylet handle 70 may be coupled to plunger body 52 such that shaft 68 extends through at least a portion of liner tube 14 during the insertion of liner tube 14 through port 24 and delivery shaft 20. Positioning stylet 34 within liner tube 14 may add rigidity to liner tube 14, which may help in the insertion. Stylet handle 70 may also help to ensure that shaft 68 of stylet 34 may be removed from liner tube 14 and plunger 28 (after insertion of liner tube 14 or after cleaning/breaking up a clog within liner tube 14).

In one aspect, and as shown in FIGS. 1 and 2, plunger body 52 may be at least partially transparent. Although not shown, plunger housing 56 may also be at least partially transparent. As such, an operator may visually observe the relative positioning of plunger body 52 relative to plunger housing 56. The operator may also visually observe the relative position of plunger body 52 relative to plunger housing 56 via the position of pin 60 in pin track 62. Moreover, the operator may visually observe the position of shaft 68 of stylet 34 within both plunger body 52 and plunger housing 56, either through one or more partially transparent components or via the position of a distal edge of handle 70 relative to a proximal edge of plunger hub 54.

Medical device 16 will be described as a laser fiber. However, it is understood that medical device 16 may be any type of medical device used in conjunction with insertion device 12 to delivery medical therapy to a target site inside a subject. For example, medical device 16 may alternatively be a retrieval basket, a snare, forceps, and/or a needle. Additionally, although not shown, medical device 16 may include one or more of a sheath, an insulation layer, a coating layer, etc.

As mentioned, medical device 16 may be coupled to insertion device 12 via fitting 30. Medical device 16 may be coupled to a radial exterior of delivery shaft 20 via coupling tube 32. For example, as discussed in detail below, coupling tube 32 may include a proximal opening (not shown) and a distal opening 74 (FIG. 1) with a lumen extending therebetween configured to receive medical device 16. Coupling tube 32 may be coupled to delivery shaft 20 via an adhesive, a plurality of rings of material (e.g., an elastic material, a heat-shrink material, etc.). In one aspect, medical system 10 may include a loop 76 of elastic or heat-shrink material coupled near the distal end of coupling tube 32, such that the distal end of coupling tube 32 may be coupled to delivery shaft 20.

Figure 3:
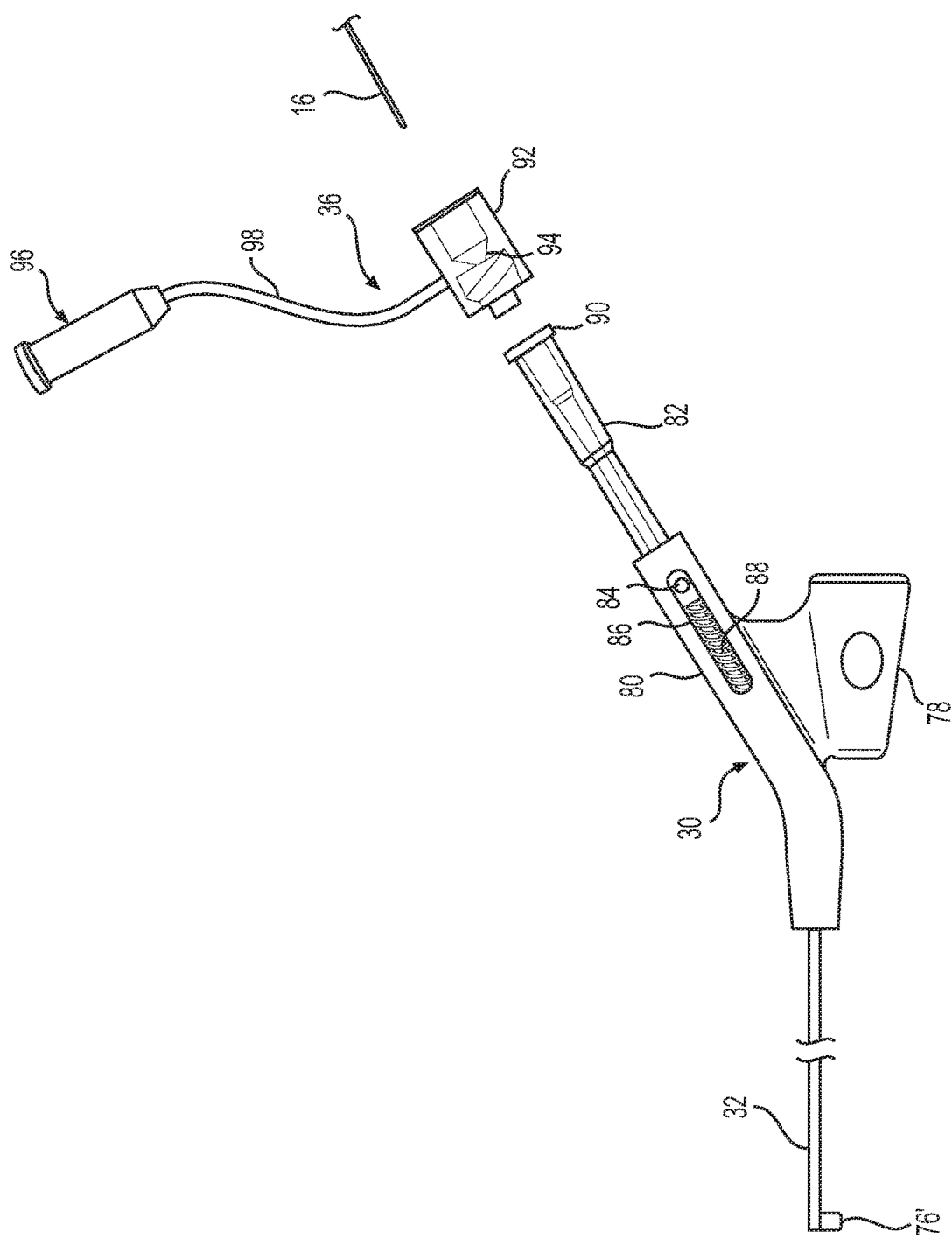
FIG. 3 illustrates another portion of the medical system of FIG. 1, according to aspects of the present disclosure.

As shown in FIG. 3, fitting 30 may include a coupling portion 78 that may surround a portion of delivery shaft 20. Fitting 30 may be integrally formed with insertion device 12, or may be coupled to distal portion 38, for example, via an adhesive, a threaded coupling, a friction fit, etc. Additionally, fitting 30 may include a fitting body 80, which may surround a portion of medical device 16. In one aspect, a fitting plunger 82 may surround a portion of medical device 16. For example, a distal end of fitting plunger 82 may be secured and sealed to a proximal end of coupling tube 32. Fitting plunger 82 may include a fitting pin 84, which may be moveable within a fitting track 86. A fitting spring 88 may be positioned within fitting body 80, and may bias the movement of fitting plunger 82 relative to fitting body 80. Additionally, fitting spring 88 may help coupling tube 32 to flex and deflect with delivery shaft 20 based on activation of deflection lever 22 and/or the insertion or maneuvering of delivery shaft 20 to a treatment site, and may also help coupling tube 32 stay in tension or take up slack when delivery shaft 20 is in a straight (not flexed or deflected) condition. In one aspect, coupling tube 32 may also include an extension or loop 76' of elastic or flexible material coupled to the distal end of coupling tube 32, and loop 76' may then be coupled to the distal end 44 of delivery shaft 20. For example, loop 76' may fix the position of the distal end of coupling tube 32 relative to delivery shaft 20, and as delivery shaft flexes or deflects, fitting plunger 82 may move within fitting body 80, as biased by fitting spring 88. Although not shown, fitting track 86 may include one or more slots to lockably position fitting plunger 82 relative to fitting body 80, and thus lockably position coupling tube 32 relative to insertion device 12 and delivery shaft 20.

Fitting plunger 82 may be fixed around the portion of medical device 16, and may be moveable within fitting body 80 of fitting 30 to biasedly extend and retract coupling tube 32 and medical device 16. In another aspect, medical device 16 may be longitudinally movable through seal adaptor 36, fitting 30, and coupling tube 32, for example, to extend medical device 16 distally beyond coupling tube 32 to deliver laser energy to a kidney stone.

Seal adaptor 36 may be coupled to a proximal end of fitting plunger 82, for example, to a fitting plunger hub 90. Seal adaptor 36 includes an adaptor body 92 with a valve 94, for example, a one-way valve, which may receive and form a seal around medical device 16. Seal adaptor 36 also includes an adaptor port 96 and an adaptor tube 98. Adaptor tube 98 may be coupled to adaptor body 92 at a position distal to valve 94. Medical device 16 may be inserted through seal adaptor 36 and through fitting plunger 82 and coupling adaptor port 96 may be coupled to a fluid source (not shown), and a fluid (e.g., an irrigation fluid, a radiopaque fluid, etc.) may be delivered from the fluid source through adaptor port 96 and adaptor tube 98 and around medical device 16 in coupling tube 32.

In one aspect, and as shown in FIGS. 1 and 3, one or more of fitting body 80, fitting plunger 82, and seal adaptor 36 may be at least partially transparent. As such, an operator may visually observe the relative positioning of fitting plunger 82 relative to fitting body 80. Additionally, the operator may visually observe the relative positioning of fitting plunger 82 relative to fitting body 80 via the position of fitting pin 84 within fitting track 86. Moreover, the operator may visually observe the position of medical device 16 within one or more of fitting body 80, fitting plunger 82, and seal adaptor 36. The operator may also visually observe the position of medical device 16 through one or more visualization units (e.g., a camera) positioned at or within distal end 44 of delivery shaft 20.

Figure 4B:
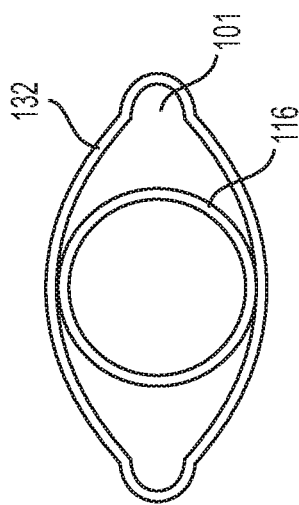
FIGS. 4A and 4B illustrate cross-sectional views of a coupling tube in a collapsed and an expanded configuration, according to aspects of the present disclosure.
Figure 4A:
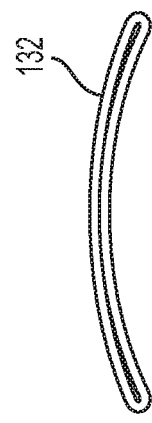

FIGS. 4A and 4B illustrate an alternative example according to the present disclosure, with similar elements to medical system 10 shown by 100 added to the reference numbers. FIGS. 4A and 4B illustrate cross-sectional views of various configurations of coupling tube 132. As shown in FIG. 4A, coupling tube 132 may include a collapsed configuration. In this collapsed configuration, coupling tube 132 may include a collapsed lumen and may be at least partially curved to surround a portion of delivery shaft 20. For example, coupling tube 132 may be in the collapsed configuration and coupled to delivery shaft 20 during the insertion and positioning of delivery shaft 20 to the treatment site.

As shown in FIG. 4B, coupling tube 132 may include an expanded configuration. In this expanded configuration, coupling tube 132 may be substantially ovular or elliptical. Coupling tube 32 may transition to the expanded configuration upon the insertion of medical device 116 within a lumen 101 of coupling tube 132. Additionally, lumen 101 of coupling tube 132 may be wider or larger than medical device 116. Accordingly, fluid may be delivered through coupling tube 132 and around medical device 116, as discussed above. Moreover, coupling tube 32 may include an inherent biasing to return to the collapsed configuration (FIG. 4A) when medical device 116 is removed from coupling tube 132. Although the collapsed and expanded configurations of coupling tube 132 are shown as curved or partially ovular, this disclosure is not so limited. Coupling tube 132 may take any appropriate shape in the collapsed and expanded configurations.

Figure 5B:
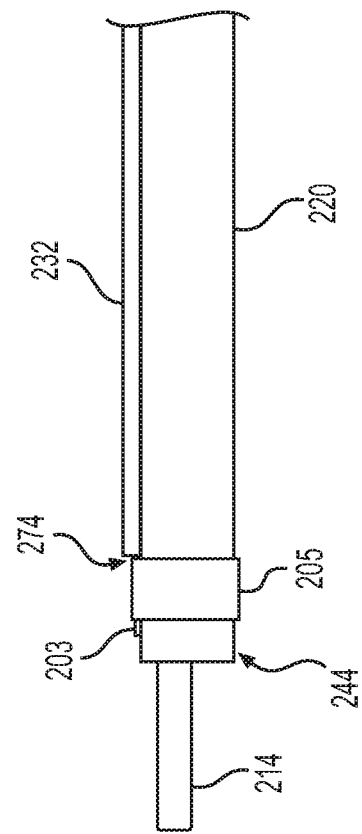
FIGS. 5A and 5B illustrate a distal end of the coupling tube in an isolated view and as coupled to the distal end of the medical system, according to aspects of the present disclosure.
Figure 5A:
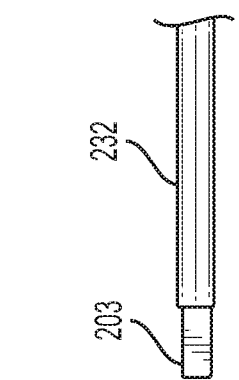

FIGS. 5A and 5B illustrate an alternative example according to the present disclosure, with similar elements to medical system 10 shown by 200 added to the reference numbers. FIGS. 5A and 5B illustrate additional aspects of coupling tube 232. FIG. 5A illustrates a distal portion of coupling tube 232. In particular, coupling tube 232 may include a distal flap 203. In one aspect, distal flap 203 may be formed by cutting, skiving, or otherwise removing a distal end portion of coupling tube 232. Distal flap 203 may then form a substantially flat piece of material extending from coupling tube 232, and the distal end of coupling tube 232 is open to form distal opening 274 (FIG. 5B), such that medical device 16 may extend distally beyond coupling tube 232 and/or deliver treatment to the treatment site.

As shown in FIG. 5B, coupling tube 232 may be positioned along and secured to a distal portion of delivery shaft 220. For example, a loop 205 may surround distal flap 203 and delivery shaft 220 near distal end 244. Loop 205 may be a ring of material (e.g., an elastic material, a heat-shrink material, etc.). Although loop 205 is shown as a separate element, in one aspect loop 205 may be integrally formed with coupling tube 232 and distal flap 203.

FIG. 5B also illustrates the extension of liner tube 214 from distal end 244 of delivery shaft 220. As discussed above, action on plunger body 52 may extend liner tube 214 relative to insertion device 12 and delivery shaft 220. For example, with suction being delivered through liner tube 214, a clog may form at distal opening 46 or near distal end 244 of delivery shaft 220. An operator may extend liner tube 214 to break up the clog or push the clogged material out of distal opening 46. Furthermore, the operator may extend liner tube 214 to apply suction to material or a treatment site distally beyond distal end 244.

FIGS. 6A-6D illustrate alternative examples according to the present disclosure, with similar elements to medical system 10 shown by 300 added to the reference numbers. In particular, FIGS. 6A-6C illustrate a coupling tube 332 and a mechanism to couple coupling tube 332 to a distal end 344 of delivery shaft 320. FIG. 6A is a side view of coupling tube 332. As shown, coupling tube 332 includes a skived portion 311. Skived portion 311 is proximal to the distal end of coupling tube 332 and forms a flap 313. Flap 313 is open along a portion of the longitudinal length of coupling tube 332. Coupling tube 332 also includes a closed distal portion 315. As shown in FIG. 6A, distal portion 315 may be wider than the proximal portion of coupling tube 332, and flap 313 may transition from the narrower proximal portion of coupling tube 332 to the wider distal portion 315. In one aspect, distal portion 315 of coupling tube 332 may be the same diameter as a proximal portion of coupling tube 332, and the proximal portion of coupling tube 332 may transition from a flatten or collapsed state to an expanded state with the same diameter as distal portion 315.

Additionally, a portion of a tube insert 317 may be coupled or otherwise positioned within distal portion 315. For example, tube insert 317 may include an outer diameter approximately the same size or slightly smaller than an inner diameter of distal portion 315. Tube insert 317 may be more rigid than coupling tube 332. For example, tube insert 317 may be formed of a stainless steel hypodermic tube or another appropriate material, and may include a wall thickness of approximately 0.0025 inches. Although not shown, the outer surface of tube insert 317 may be tapered, sand blasted, grooved, textured, barbed, or otherwise modified to help insert and maintain distal portion 315 and tube insert 317 into distal opening 346 at distal end 344 of delivery shaft 320.

In another aspect, distal portion 315 may be cut longitudinally, with the cut portions positioned around a portion of tube insert 317. In any of the above aspects, at least distal portion 315 of coupling tube 332 may be formed of a heat-shrink material, and may be heat-shrunk around a portion of tube insert 317. Alternatively or additionally, an adhesive may be used to help couple distal portion 315 and tube insert 317.

As shown in FIG. 6B, flap 313 may be bent approximately 180 degrees. In this bent arrangement, distal opening 374 may be approximately aligned with a distal end (formerly a proximal end) of distal portion 315 and tube insert 317. Distal portion 315 and tube insert 317 may be positioned within distal opening 346 at distal end 344 of delivery shaft 320. In one aspect, an insertion tool 319 may be used to couple distal portion 315 and tube insert 317 into distal opening 346 at distal end 344 of delivery shaft 320. It is noted that various aspects of delivery shaft 320 (e.g., camera and illumination source 48) are omitted for clarity. Insertion tool 319 may include an atraumatic tip and a wider handle portion. The atraumatic tip may be inserted within tube insert 317, and may help securely couple distal portion 315 and tube insert 317 within distal opening 346. As shown in FIG. 6C, distal opening 374 may be aligned with or just proximal to distal opening 346, and coupling tube 332 may be securely coupled to delivery shaft, with tube insert 317 helping to secure distal portion 315 within distal opening 346. Although not shown, liner tube 14 and stylet 34 may be inserted through delivery shaft 320 and may be longitudinally movable through distal opening 346 (e.g., radially within distal portion 315 and tube insert 317). Furthermore, one or more loops 76, 205 (FIGS. 1 and 5B) may be used to attach coupling tube 332 to delivery shaft 320, for example, at various positions along a longitudinal length of delivery shaft 320.

FIG. 6D illustrates a coupling tube 332 and another mechanism to couple coupling tube 332 to distal end 344 of delivery shaft 320. FIG. 6D is similar to FIG. 6C, but with distal portion 315' being thicker or wider than distal portion 315. In this embodiment, for example, because distal portion 315' is thicker or wider than tube insert 317 and distal opening 346, only tube insert 317 may be inserted into distal opening 346. In this aspect, delivery shaft 320 may maintain a larger inner diameter to allow for a larger liner tube 14 to pass through and remove a greater volume of fluid or stone dust, larger stones, or a greater amount of debris. Furthermore, with distal portion 315' external to distal opening 346, distal portion 315' may be gripped by the operator to assist in removing tube insert 317 from distal opening 346. In this example, insertion tool 319 may be used to help couple tube insert 317 within distal opening, with distal portion 315' remaining distal to distal opening 346.

Figure 7:
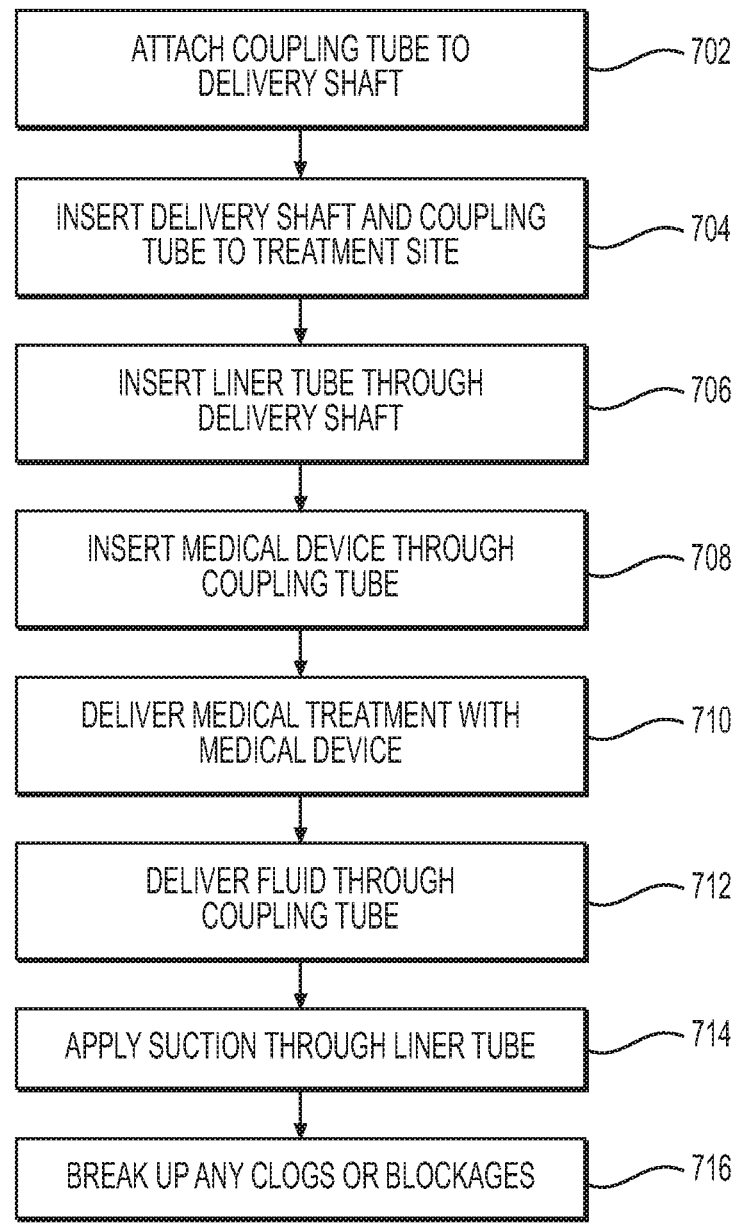
FIG. 7 provides a flowchart depicting an exemplary method for breaking up and removing a hardened mass from a body cavity, according to aspects of the present disclosure.

FIG. 7 depicts a flow diagram of a method 700 that may be performed with any of the medical devices and systems discussed herein. For example, a step 702 includes attaching coupling tube 32, 132, 232, 332 to delivery shaft 20, 220, 320. Attaching coupling tube 32 may include one or more loops 76, 76', 205 (FIGS. 1, 3, 5A, and 5B) around coupling tube 32, 132, 232, 332 (or flap 203) and delivery shaft 20, 220, 320. Alternatively or additionally, step 702 may include distal portion 315 and tube insert 317, or only tube insert 317, being coupled within distal opening 346 (FIGS. 6A-6B). Moreover, step 702 may include coupling portion 78 of fitting 30 being attached around a portion of delivery shaft 20, as discussed above with respect to FIGS. 1 and 3.

Next, a step 704 includes inserting delivery shaft 20, 220, 320 and coupling tube 32, 132, 232, 332 to the treatment site. Step 704 may include an insertion guidewire or an other appropriate guidance or delivery element. As shown in FIG. 4A, coupling tube 132 may be in a collapsed configuration during the insertion (without medical device 116) such that coupling tube 132 does not significantly increase a cross-sectional profile of delivery tube 20, 220, 320 during insertion and positioning. Moreover, an operator may use deflection lever 22 to position distal end 44, 244, 344 of delivery shaft 20, 220, 320 to the treatment site. In one aspect, a proximal portion of coupling tube 32, 132, 232, 332 is coupled to delivery shaft 20, 220, 320 via fitting 30 and spring 88, so coupling tube 32, 132, 232, 332 may deflect with delivery shaft 20, 220, 320, with a reduced risk of breaking or disconnecting from delivery shaft 20, 220, 320.

A step 706 includes inserting liner tube 14 through delivery shaft 20. Liner tube 14 may be inserted through port 24, and secured via connector 26 and a proximal end of liner tube 14 may be coupled to plunger 52, as discussed above. During insertion, shaft 68 of stylet 34 may be positioned within at least a portion of liner tube 14 for additional support. Once liner tube 14 is inserted within delivery shaft 20 plunger hub 52 may be coupled to a suction source (not shown). Alternatively, step 706 may be performed as part of step 702 before delivery shaft 20 and coupling tube 32 are inserted to the treatment site.

In step 708, medical device 16, 116 may be inserted through coupling tube 32, 132, 232, 332. Medical device 16, 116 may be inserted to a position distal to, aligned with, or proximal to distal end 74, 274, 374 of coupling tube 32, 132, 232, 332. Medical device 16, 116 may be inserted through seal adaptor 36 and fitting plunger 82 such that valve 94 in adaptor body 92 forms a seal around medical device 16, 116. Additionally, as shown in FIGS. 4A and 4B, inserting medical device 116 through coupling tube 132 may expand coupling tube 132 from a collapsed configuration to an expanded configuration, which may include lumen 101.

A step 710 includes delivering medical treatment with medical device 16. For example, the proximal end of medical device 16 may be coupled to an energy source. The distal end of medical device 16 may be extended to be aligned with or extend distally beyond distal opening 74, 274, 374 (e.g., by moving fitting plunger 82 relative to fitting body 80), and may deliver energy to a kidney stone or other hardened mass. Step 710 may also include further positioning of distal end 44, 244, 344 in order to align the delivered energy with the kidney stone or hardened mass, which may include using visualization through camera and/or illumination source 48, deflection lever 22, fitting plunger 82, etc.

Next, a step 712 includes delivering fluid through coupling tube 32, 132, 232, 332. As discussed above, a fluid source may be coupled to adaptor port 96 such that fluid may be delivered through adaptor tube 98, fitting plunger 82, and through coupling tube 32, 132, 232, 332, for example, through lumen 101. The fluid may be irrigation fluid, radiopaque fluid, etc. The fluid source may be selectively activated (e.g., by a button, foot pedal, etc.), may be a gravity-assisted irrigation bag, or other fluid source, and may help agitate the kidney stone or hardened mass as it is broken up with the energy from medical device 16, 116.

A step 714 includes applying suction through liner tube 14. As mentioned, the proximal end of plunger body (e.g., plunger hub 54) may be coupled to a suction source. The suction source may be selectively activated (e.g., by a button, foot pedal, etc.) to remove fluid (e.g., excess fluid, fluid carrying stone dust, etc.) and pieces of the kidney stone or hardened mass, for example, stone dust. Step 714 may also include selectively positioning liner tube 14 relative to distal opening 46 by positioning pin 60 on plunger 52 in one of slots 66A-66C of pin track 62.

A step 716 may include breaking up or clearing any clogs or blockages that may form in liner tube 14. For example, during step 714 above, stone dust or other particulate matter may collect in distal opening 46 and form a clog or blockage. In this aspect, an operator may extend liner tube 14, using plunger 52, distally beyond distal opening 46 to break up the clog or blockage or push the clogged material distally out of delivery shaft 20. In another aspect, stone dust or other particulate matter may collect in liner tube 14. In this aspect, shaft 68 of stylet 34 may be extended through at least a portion of liner tube 14 to break up or clear the clog or blockage. In either aspect, suction may then be applied again, as in step 714, or the operator may deliver energy via medical device 16, 116 to the material that formed the clog or blockage to further break up the material. Furthermore, the operator may remove liner tube 14 from the working channel of insertion device 12 with the clog retained within liner tube 14. The operator may then attempt to remove the clog from liner tube 14 with liner tube 14 external to the patient. If successful, the operator may re-insert liner tube 14 into insertion device 12. Alternatively, the operator may insert a different or new liner tube 14 through insertion device 12, or the operator may continue the procedure without a liner tube positioned within insertion device 12.

Steps 710-716 may be repeated as many times as necessary to break up and remove the kidney stone(s) or other hard material from treatment site. Furthermore, distal end 44, 244, 344 of delivery shaft 20, 220, 320 may be repositioned (e.g., using deflection lever 22) as many times as necessary. Once the kidney stone(s) or other material has been removed from the treatment site, which may be confirmed via camera and/or illumination source 48 or other methods, the operator may remove medical system 10 from the treatment site.

The systems, devices, and methods discussed herein may help an operator to quickly and safely deliver medical treatment to a treatment site, for example, to break up and remove kidney stones or other hard material. As discussed above, once medical system 10 is positioned at the treatment site, there is no need to remove insertion device 12 and/or medical device 16 to deliver fluid, apply suction, or otherwise treat the treatment site. During insertion, coupling tube 32, 132, 232, 332 may not substantially increase a cross-sectional area of medical system 10, which may reduce the likelihood of injury to the patient, as discussed with respect to FIGS. 4A and 4B. Additionally, with coupling tube 32, 132, 232, 332 coupled to delivery shaft 20 and insertion device 12 via fitting 30 and spring 80, the operator may deflect delivery shaft 20 with a reduced risk of disconnecting or interrupting connection to coupling tube 32. Medical system 10 allows the operator the ability to break up clogs or blockages that may form in delivery shaft 20 as a result of the suction. For example, the operator may extend or retract liner tube 14 using plunger 52, or the operator may insert stylet 34 through liner tube 14, without removing delivery shaft 20 or another component of medical system 10. In some aspects, medical system 10 allows the operator to lock positions of plunger body 52 relative to plunger housing 56 or fitting plunger 82 relative to fitting body 80, and thus lock the positions of liner tube 14 and coupling tube 32 relative to delivery shaft 20.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical system, comprising:
an insertion device including a delivery shaft with an internal lumen;

a coupling tube coupled to the delivery shaft via a fitting and configured to receive a medical device;

a coupling tube plunger coupled to a proximal end of the coupling tube, wherein the fitting includes a fitting housing with a spring biasing the coupling tube plunger;

a liner tube inserted through the internal lumen of the delivery shaft; and an adaptor coupled to a proximal end of the coupling tube plunger, wherein the adaptor is configured to form a one-way seal around the medical device.

2. The medical system of claim 1, wherein the coupling tube includes a collapsed configuration and an expanded configuration, wherein the coupling tube is configured to transition to the expanded configuration upon receiving the medical device, and wherein the coupling tube is configured to transition to the expanded configuration during delivery of a fluid and to transition to the collapsed configuration during delivery of suction.

3. The medical system of claim 1, wherein the fitting housing includes a slot, and wherein the coupling tube plunger includes a pin configured to move within the slot.

4. The medical system of claim 1, wherein a distal end of the coupling tube includes a distal flap, and further including a loop surrounding a distal portion of the delivery shaft and the distal flap.

5. The medical system of claim 1, further including one or more loops surrounding one or more portions of the delivery shaft and the coupling tube, wherein the one or more loops are formed of a heat-shrink or elastic material.

6. The medical system of claim 1, wherein a distal end of the coupling tube includes a skived portion and a distal portion, wherein the distal portion of the coupling tube is coupled to a tube insert, and wherein the tube insert is positioned within a distal opening of the delivery shaft.

7. The medical system of claim 6, further including a tube insert positioned within the distal portion of the coupling tube, wherein the tube insert is more rigid than the coupling tube.

8. The medical system of claim 1, wherein the insertion device includes a port, and wherein the liner tube is inserted through and coupled to the port via a connector that forms a seal around the port.

9. The medical system of claim 8, wherein the connector includes a liner tube plunger and a liner tube plunger housing, and wherein the liner tube plunger is longitudinally movable within at least a portion of the liner tube plunger housing.

10. The medical system of claim 9, wherein the liner tube plunger housing includes a spring biasing the liner tube plunger.

11. The medical system of claim 10, wherein the liner tube plunger housing includes a track, and wherein the liner tube plunger includes a pin configured to move within the track.

12. The medical system of claim 11, wherein the track in the liner tube plunger housing includes a longitudinally extending channel with one or more slots extending from the channel.

13. The medical system of claim 1, further including a stylet configured to extend through at least a portion of the liner tube.

14. A medical system, comprising:

an insertion device including a delivery shaft with an internal lumen;

a coupling tube coupled to the delivery shaft and configured to receive a medical device, wherein the coupling tube is configured to transition between a collapsed configuration and an expanded configuration upon receiving the medical device and wherein a distal end of the coupling tube includes a skived portion and a distal portion; and a tube insert coupled to the distal portion of the distal end of the coupling tube and is positioned within a distal opening of the delivery shaft, wherein the tube insert is more rigid than the coupling tube, and wherein the coupling tube is coupled to an exterior of the delivery shaft.

15. The medical system of claim 14, wherein the coupling tube is coupled to the delivery shaft via a fitting;

wherein a proximal end of the coupling tube is coupled to a coupling tube plunger; wherein the fitting includes a fitting housing with a spring biasing the coupling tube plunger; and wherein the fitting housing includes a slot, and wherein the coupling tube plunger includes a pin configured to move within the slot.

* * * * *